(12) United States Patent
Di Nicolo' et al.

(10) Patent No.: US 11,672,890 B2
(45) Date of Patent: Jun. 13, 2023

(54) MEDICAL DEVICES

(71) Applicant: SOLVAY SPECIALTY POLYMERS ITALY S.P.A., Bollate (IT)

(72) Inventors: Emanuele Di Nicolo', Gorla Minore (IT); Silvia Rita Petricci, Bresso (IT); Pasquale Campanelli, Limbiate (IT); Marco Beltramin, Senago (IT)

(73) Assignee: SOLVAY SPECIALTY POLYMERS ITALY S.P.A., Bollate (IT)

( * ) Notice: Subject to any disclaimer, the term of this patent is extended or adjusted under 35 U.S.C. 154(b) by 414 days.

(21) Appl. No.: 16/762,912

(22) PCT Filed: Nov. 21, 2018

(86) PCT No.: PCT/EP2018/082018
§ 371 (c)(1),
(2) Date: May 8, 2020

(87) PCT Pub. No.: WO2019/101771
PCT Pub. Date: May 31, 2019

(65) Prior Publication Data
US 2020/0360570 A1    Nov. 19, 2020

(30) Foreign Application Priority Data

Nov. 23, 2017 (EP) .................................. 17203351

(51) Int. Cl.
| *A61L 29/06* | (2006.01) |
| *C08G 18/50* | (2006.01) |
| *C08L 27/06* | (2006.01) |
| *C08L 75/04* | (2006.01) |
| *C08G 18/32* | (2006.01) |
| *C08G 18/76* | (2006.01) |
| *C08G 18/66* | (2006.01) |

(52) U.S. Cl.
CPC .......... *A61L 29/06* (2013.01); *C08G 18/3206* (2013.01); *C08G 18/5015* (2013.01); *C08G 18/6674* (2013.01); *C08G 18/7671* (2013.01); *C08L 27/06* (2013.01); *C08L 75/04* (2013.01)

(58) Field of Classification Search
CPC ... A61L 29/06; C08G 18/222; C08G 18/3206; C08G 18/4854; C08G 18/5015; C08G 18/6674; C08G 18/7671; C08L 27/06; C08L 75/04; C08L 75/08; C09D 175/04
See application file for complete search history.

(56) References Cited

U.S. PATENT DOCUMENTS

| 4,841,007 | A | 6/1989 | Zdrahala et al. |
| 4,935,480 | A | 6/1990 | Zdrahala et al. |
| 5,332,798 | A | 7/1994 | Ferreri et al. |
| 8,603,070 | B1 | 12/2013 | Lareau et al. |
| 2003/0139540 | A1 | 7/2003 | Turri et al. |
| 2011/0009799 | A1 | 1/2011 | Mullick et al. |
| 2016/0310641 | A1* | 10/2016 | Santerre ............... C09D 175/04 |

FOREIGN PATENT DOCUMENTS

| EP | 1864685 | A1 | 12/2007 |
| JP | H0263464 | A | 3/1990 |
| JP | 2003048947 | A | 2/2003 |
| JP | 2012506932 | A | 3/2012 |
| WO | 9706195 | A1 | 2/1997 |
| WO | 2010049365 | A2 | 5/2010 |
| WO | WO2017/211870 | * | 12/2017 |
| WO | 2018029131 | A1 | 2/2018 |
| WO | 2018029133 | A1 | 2/2018 |

OTHER PUBLICATIONS

Office Action issued in corresponding JP Application No. 2020-527792 with English translation dated Sep. 13, 2022 (8 pages).

* cited by examiner

*Primary Examiner* — Yan Lan
(74) *Attorney, Agent, or Firm* — Osha Bergman Watanabe & Burton LLP

(57) ABSTRACT

The present invention relates to medical devices, such as catheters, made from a composition comprising at least one (per) fluoropolyether polymer; methods for the manufacture thereof; and their uses and applications in medicine.

15 Claims, No Drawings

MEDICAL DEVICES

CROSS-REFERENCE TO RELATED PATENT APPLICATIONS

This application is a U.S. national stage entry under 35 U.S.C. § 371 of International Application No. PCT/EP2018/082018 filed Nov. 21, 2018, which claims priority to European patent application No. 17203351.6, filed on Nov. 23, 2017. The entire contents of these applications are explicitly incorporated herein by this reference.

TECHNICAL FIELD

The present invention relates to medical devices made from a composition comprising at least one (per)fluoropolyether polymer; methods for the manufacture thereof; and their uses and applications in medicine.

BACKGROUND ART

Medical tubing (also referred to as "catheters") are thin tubes made from medical grade materials, which can be either inserted in the body to treat diseases or perform surgical procedures or used in the extracorporeal treatment of a patient's body fluid. Indeed, on the one hand, medical tubing are designed to be inserted, either temporarily or permanently, into a body cavity, duct or vessel, in order to allow drainage or administration of fluids or gases, and access by surgical instruments. On the other hand, for the extracorporeal treatment, medical tubing are designed to connect external systems, which extract the patient's blood to the dialysis device.

The materials and the process for the manufacture of the medical tubing are selected and tailored based on the final use for which the tubing is intended. Typically used polymeric materials include silicone rubbers, nylons, hydrogenated polyurethane, polyethylene terephthalate, latex and thermoplastic elastomers.

Silicone rubbers are the most common choice, as they are inert and unreactive to body fluids. However, their mechanical properties are weak, such that fractures can occur when the medical tubing is used.

One of the drawback of the use of medical tubing, notably when they are used for prolonged periods of time, is the aggregation of platelets on their surface, which can lead to the formation of thrombus and consequently to complications including stream infection and thrombosis.

The improvement of the biocompatibility of the medical tubing with the body fluids, as well as the reduction of the formation of thrombi, have been subject to research efforts. For example, biologically active molecules able of permanent binding the surface of the polymeric material from which the medical tubing is manufactured have been studied.

WO 97/06195 (SANTERRE PAUL J.) discloses a composition comprising a polymer, preferably a polyurethane, and a macromolecule having (i) a central portion of a segmented block oligomeric copolymer comprising at least one polar hard segment, and (ii) terminal poly-fluoro oligomeric groups, wherein said macromolecule acts as surface-modifying with the aim of improving the resistance to enzyme degradation.

U.S. Pat. No. 8,603,070 (ANGIODYNAMICS, INC.) provides catheter compositions comprising a fluoropolymer additive, which is preferably a fluoroalkyl fluoropolymer characterized by terminal polyfluoro oligomeric groups.

Both the above documents disclose a oligomeric fluoro-alcohol of formula $H—(OCH_2CH_2)_n—(CF_2)_m—CF_3$ wherein n ranges from 1 to 10 and m ranges from 1 to 20.

US 20160310641 (INTERFACE BIOLOGICS INC.; ANGIODYNAMICS, INC.) relates to admixtures comprising a thermoplastic polyurethane base polymer and a fluorinated additive, and their use in the manufacture of medical devices, such as catheters. The fluorinated additive can be formed by (i) reacting a hard segment diisocyanate with a soft segment diol to form a pre-polymer and (ii) reacting the pre-polymer with a polyfluoroalkyl alcohol. The polyfluoroalkyl alcohol can be selected for example from 1H,1H,2H,2H-perfluoro-1-decanol; 1H,1H,2H,2H-perfluoro-1-octanol; 1H,1H,5H-perfluoro-1-pentanol; and 1H,1H-perfluoro-1-butanol. The admixture disclosed in this document is said to be useful to impart haemocompatibility to a surface and/or to provide a surface to a dwelling device having reduced thrombogenicity.

EP 1864685 A (SOLVAY SOLEXIS S.P.A.) discloses a process for the manufacture of a medical implant, said process comprising:

reacting a mixture of non-functional, mono-functional and bi-functional perfluoropolyethers comprising hydroxyl terminal groups with suitable reactants for producing a thermoplastic elastomer;

moulding the so-obtained thermoplastic elastomer for yielding at least a part of the medical implant. Medical implants are notably selected from blood vessel prosthesis, cardiac surgery device, angioplastic device, intraluminal prosthesis, for body passageways other than blood vessels, infusion therapy device, haemodialysis implant and wound dressing device.

This document however neither discloses nor provides any hint to a composition wherein the thermoplastic elastomer is used as additive.

U.S. Pat. No. 4,935,480 (ZDRAHALA RICHARD J. ET AL.) discloses a thermoplastic fluorinated polyetherurethanes, a method for its preparation and medical devices fabricated from this material. The fluorinated monomer described in this document is preferably a polyether glycol comprising a perfluorinated alkyl group having from 1 to 12 carbon atoms. This document neither discloses nor suggests the use of (per)fluoropolyether polymers (PFPE) as monomer for the manufacture of the polyetherurethane polymer.

WO 2018/029133 (SOLVAY SPECIALTY POLYMERS ITALY S.P.A.) discloses a composition comprising at least one aromatic polymer, notably selected from poly(arylene sulfide) (PAS) polymers and aromatic sulfone polymers, at least one fluorinated polyurethane polymer, and at least one further ingredient. This document also discloses that the above mentioned composition is useful for the manufacture of dense film and porous membrane.

WO 2018/029131 (SOLVAY SPECIALTY POLYMERS ITALY S.P.A.) discloses a porous membrane prepared from a composition comprising at least one fluorinated polyurethane polymer.

SUMMARY OF INVENTION

The Applicant faced the problem of providing a composition suitable for the manufacture of a medical device, notably a medical tubing (herein after also referred to as "catheter") suitable for use both within the patient's body and for the treatment of biological fluids outside the patient's body, which is biocompatible while showing good mechanical properties.

The Applicant surprisingly found that the above problem can be solved by a composition comprising a melt-processable polymer and at least one fluorinated thermoplastic polyurethane polymer (F-TPU) comprising (per)fluoropolyether moiety(ies).

Thus, in a first aspect the present invention relates to a composition [composition (C)] comprising:

(I) at least one melt-processable polymer, and (II) at least one fluorinated polyurethane polymer [F-TPU polymer] comprising recurring units derived from:

[monomer (b)] at least one hydroxy-terminated (per)fluoropolyether polymer [PFPE polymer];

[monomer (c)] at least one aromatic, aliphatic or cycloaliphatic diisocyanate; and

[monomer (d)] at least one aliphatic, cycloaliphatic or aromatic diol having from 1 to 14 carbon atoms;

wherein said melt-processable polymer is different from said F-TPU polymer.

According to a preferred embodiment, said F-TPU polymer further comprises recurring units derived from [monomer (a)] at least one diol selected from the group comprising poly-ether type diol, poly-ester type diol, polybutadien-diol and polycarbonate-diol.

According to a preferred embodiment, said at least one melt-processable polymer is a non-fluorinated polymer.

According to a more preferred embodiment, said at least one melt-processable polymer is selected in the group comprising, preferably consisting of, poly(vinyl chloride) (PVC), polyolefins and silicones (also referred to as polysiloxanes).

In a second aspect, the present invention relates to an article made from composition (C) as defined above.

According to a preferred embodiment, said article is a medical device, notably a medical tubing.

In a third aspect, the present invention relates to the use of the medical tubing according to the present invention:

to administer a medical substance to at least one cavity, duct or vessel of the human or animal body; or to perform a surgical procedure in at least one cavity, duct or vessel of the human or animal body; or in the extracorporeal treatment of a patient's body fluid.

In a fourth aspect, the present invention relates to a method for administering a medical substance to at least one cavity, duct or vessel of the human or animal body, said method comprising the use of the medical tubing according to the present invention.

In a fifth aspect, the present invention relates to a method for performing a surgical procedure in at least one cavity, duct or vessel of the human or animal body, said method comprising the use of the medical tubing according to the present invention.

In a sixth aspect, the present invention relates to a method for the extracorporeal treatment of a patient's body fluid, preferably of blood, said method comprising the use of the medical tubing according to the present invention.

Surprisingly, the Applicant found that when the F-TPU polymer is provided in admixture with a melt-processable polymer typically used in the manufacture of medical devices, such as notably medical tubing, the anti-thrombogenic properties of the final medical device are not negatively affected. Without being bound by any theory, the Applicant believes that this is due to the water- and oleo-repellency properties provided by the F-TPU polymer to the surface of the medical device.

DESCRIPTION OF EMBODIMENTS

For the purpose of the present description and of the following claims:

the use of parentheses before and after symbols or numbers identifying compounds, chemical formulae or parts of formulae has the mere purpose of better distinguishing those symbols or numbers from the rest of the text and hence said parentheses can also be omitted;

the expression "melt-processable" is intended to indicate polymers that can be processed (i.e. fabricated) into shaped articles (such as tubes, pipes, and the like) at a temperature higher than their glass transition temperature ($T_g$). The expression "melt-processable polymer" is herein intended to comprise (A) elastomeric polymers, before the curing step, (B) (semi)crystalline polymers and (C) polymers comprising both elastomeric and semi-crystalline segments;

the term "elastomer" is intended to indicate amorphous polymers or polymers having a low degree of crystallinity (crystalline phase less than 20% by volume) and a glass transition temperature value ($T_g$), measured according to ASTM D3418, below room temperature. More preferably, the elastomer according to the present invention has a $T_g$ below 10° C., even more preferably below 5° C., as measured according to ASTM D-3418;

the term "(per)fluoropolyether" is intended to indicate a "fully or partially fluorinated polyether" polymer;

the expression "(per)fluoropolyoxyalkylene chain" is intended to indicate a partially or fully fluorinated, straight or branched, polyoxyalkylene chain;

the term "catheter" used as synonym of "medical tubing" and it is intended to indicate a medical device in the form of a hollow cylinder, preferably of elongated form, that can be either inserted in the body to treat diseases or perform surgical procedures or used in the extracorporeal treatment of a patient's body fluid.

Preferably, when the melt-processable polymer is (A) at least one elastomeric polymer before the curing step, it is selected from the group comprising, more preferably consisting of, polyolefin-based elastomer (POBE) and silicones (polysiloxanes).

Preferably, when the melt-processable polymer is (B) at least one (semi)crystalline polymer, it is selected from the group comprising, more preferably consisting of, poly(vinyl chloride) (PVC), polyethylene (PE) and polypropylene (PP).

Preferably, said composition (C) comprises said melt-processable polymer in an amount of at least 60 wt. %, more preferably of at least 80 wt. %, and even more preferably of at least 85 wt. % based on the total weight of said composition (C).

Preferably, said composition (C) comprises said melt-processable polymer in an amount of at most 99.99 wt. %, more preferably of at least 98 wt. %, and even more preferably of at most 96 wt. % based on the total weight of said composition (C).

Preferably, the F-TPU polymer is a block copolymer, i.e. a polymer comprising blocks (also referred to as "segments"), each block comprising recurring units deriving from optional monomer (a), monomer (b), monomer (c) or monomer (d), as defined above.

Preferably, said F-TPU polymer has a weight average molecular weight of from 30,000 to about 150,000 Da, determined by means of gel permeation chromatography (GPC) technique.

Advantageously, the high molecular weight of the F-TPU polymer guarantees that the polymer does not release fluorinated molecules when contacted with body fluids.

Preferably, said F-TPU polymer has a melting point ($T_m$) of from about 120° C. to about 240° C.

When present, said at least one monomer (a) has an average number molecular weight of from 500 to 4,000 Da, more preferably of from 1,000 to 4,000.

Preferably, said optional at least one monomer (a) is selected in the group comprising poly(ethylene)glycol, poly (propylene)glycol, poly(tetramethylene)glycol (PTMG), poly(1,4-butanediol)adipate, poly(ethandiol-1,4-butanediol) adipate, poly(1,6-hexanediol-neopentyl)glycol adipate, polycaprolactone-diol (PCL) and polycarbonate-diol. Poly(tetramethylene)glycol, poly-caprolactone-diol and polycarbonate-diol being particularly preferred.

Preferably, said at least one monomer (b) is a hydroxy-terminated (per)fluoropolyether polymer [PFPE polymer], i.e. a polymer comprising a (per)fluoropolyoxyalkylene chain [chain $(R_{pf})$] having two chain ends, wherein one or both chain ends terminates with at least one —OH group.

Preferably, at least one chain end of said chain $(R_{pf})$ terminates with a group of formula:

$$—CH_2(OCH_2CH_2)_t—OH \quad (I)$$

wherein
t is 0 or from 1 to 5.

More preferably, both chain ends of said chain $(R_{pf})$ terminate with a group of formula (I) as defined above.

Preferably, said chain $(R_{pf})$ is a chain of formula:

wherein
z1 and z2, equal or different from each other, are equal to or higher than 1;

X# and X*, equal or different from each other, are —F or —CF$_3$, provided that when z1 and/or z2 are higher than 1, X# and X* are —F;

D and D*, equal or different from each other, are an alkylene chain comprising from 1 to 6 and even more preferably from 1 to 3 carbon atoms, said alkyl chain being optionally substituted with at least one perfluoroalkyl group comprising from 1 to 3 carbon atoms;

$(R_f)$ comprises, preferably consists of, repeating units R°, said repeating units being independently selected from the group consisting of:

(i) —CFXO—, wherein X is F or CF$_3$;
(ii) —CFXCFXO—, wherein X, equal or different at each occurrence, is F or CF$_3$, with the proviso that at least one of X is —F;
(iii) —CF$_2$CF$_2$CW$_2$O—, wherein each of W, equal or different from each other, are F, Cl, H;
(iv) —CF$_2$CF$_2$CF$_2$CF$_2$O—;
(v) —(CF$_2$)$_j$—CFZ—O— wherein j is an integer from 0 to 3 and Z is a group of general formula —O—R$_{(f-a)}$-T, wherein R$_{(f-a)}$ is a fluoropolyoxyalkene chain comprising a number of repeating units from 0 to 10, said recurring units being chosen among the following: —CFXO—, —CF$_2$CFXO—, —CF$_2$CF$_2$CF$_2$O—, —CF$_2$CF$_2$CF$_2$CF$_2$O—, with each of each of X being independently F or CF$_3$ and T being a C$_1$-C$_3$ perfluoroalkyl group.

More preferably, chain $(R_f)$ is selected from the following formulae $(R_f\text{-a})$ to $(R_f\text{-c})$:

$(R_f\text{-a})$—(CF$_2$O)$_n$(CF$_2$CF$_2$O)$_m$(CF$_2$CF$_2$CF$_2$O)$_p$ (CF$_2$CF$_2$CF$_2$CF$_2$O)$_q$— wherein m, n, p, q are 0 or integers selected in such a way as chain R$_f$ meets the above number average molecular weight requirement, with the proviso that if, p and q are simultaneously 0, n is not 0; when m is other than 0, the m/n ratio is preferably between 0.1 and 20; when (m+n) is other than 0, (p+q)/(m+n) is preferably between 0 and 0.2;

$(R_f\text{-b})$—(CF$_2$CF(CF$_3$)O)$_a$(CF$_2$CF$_2$O)$_b$(CF$_2$O)$_c$(CF(CF$_3$) O)$_d$— wherein a, b, c, d are 0 or integers selected in such a way as chain R$_f$ meets the above number average molecular weight requirement; with the proviso that, at least one of a, c and d is not 0; when b is other than 0, a/b is preferably between 0.1 and 10; when (a+b) is different from 0 (c+d)/(a+b) preferably is between 0.01 and 0.5, more preferably between 0.01 and 0.2;

$(R_f\text{-c})$—(CF$_2$CF(CF$_3$)O)$_e$(CF$_2$O)$_f$(CF(CF$_3$)O)$_g$— wherein e, f, g are 0 or integers selected in such a way as chain R$_f$ meets the above number average molecular weight requirement; when e is other than 0, (f+g)/e is preferably between 0.01 and 0.5, more preferably between 0.01 and 0.2.

PFPE polymers wherein chain $(R_f)$ complies with formula $(R_f\text{-a})$ as defined above, wherein p and q are 0, are particularly preferred in the present invention.

In a preferred embodiment, said PFPE polymer complies with the following formula (PFPE-I):

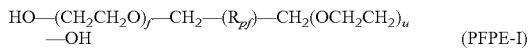

wherein
t and u are, each independently, 0 or from 1 to 5; and $R_{pf}$ is as defined above.

Preferably, said PFPE polymer has an average number molecular weight of from 400 to 10,000 Da, more preferably from 1,000 to 5,000.

In a preferred embodiment, the molar ratio between monomers (a) and monomers (b) is from 2 to 20, more preferably from 2 to 10.

In a preferred embodiment, the amount of monomers (b) is such that the F-TPU polymer comprises from 1 to 80 wt. % of fluorine, preferably from 1 to 70 wt. % based on the weight of the F-TPU polymer.

Preferably, said at least one monomer (c) has a number molecular weight of 500 Da or lower, preferably from 10 to 500 Da.

Preferably, said at least one monomer (c) is selected in the group comprising, preferably consisting of, 4,4'-methylene-diphenylene-di-isocyanate (MDI), 1,6-hexane-diisocyanate (HDI), 2,4-toluene-diisocyanate, 2,6-toluene-diisocyanate, xylylene-diisocyanate, naphthalene-diisocyanate, paraphenylene-diisocyanate, hexamethylene-diisocyanate, isophorone-diisocyanate, 4,4'-dicyclohexyl-methane-diisocyanate and cyclohexyl-1,4-diisocyanate.

MDI and HDI being particularly preferred.

Preferably, said at least one monomer (d) is selected in the group comprising, preferably consisting of, ethylene-glycol, 1,4-butanediol (BDO), 1,6-hexane diol (HDO), N,N-diethanolamine and N,N-diisopropanolaniline. BDO and HDO being particularly preferred.

In a preferred embodiment, the sum of blocks deriving from monomers (c) and (d) is from 10 to 60 wt. % based on the total weight of the F-TPU polymer.

Those skilled in the art would readily understand that blocks comprising recurring units derived from monomer (b) and monomer (a) when present are rubber-like blocks, while blocks comprising recurring units derived from monomers (c) and (d) are hard blocks.

In a preferred embodiment, at least 80% of the blocks comprising recurring units derived from said monomers (b) [blocks B] are linked, at least one of their ends, to a block comprising recurring units derived from monomers (a) [blocks A] through a block comprising recurring units derived from monomers (c) [blocks C].

In other words, at least 80% of blocks B are contained in a sequence of the following type: -[A-C-B-C]-.

Advantageously, the F-TPU polymer can be prepared according to methods known in the art, such as for example extrusion, injection moulding, casting of a solution of the monomers defined above or following the procedures disclosed in U.S. Pat. No. 5,332,798 (AUSIMONT S.P.A.).

Preferably, said composition (C) comprises said F-TPU polymer in an amount of at least 0.01 wt. %, more preferably of at least 2 wt. %, and even more preferably of at least 4 wt. % based on the total weight of said composition (C).

Preferably, said composition (C) comprises said F-TPU polymer in an amount of at most 40 wt. %, more preferably of at most 20 wt. %, and even more preferably of at most 15 wt. % based on the total weight of said composition (C).

Composition (C) optionally comprises further ingredients, which can be selected on the basis of the final intended use of the medical tubing and are biocompatible.

Said further ingredients are selected in the group comprising: plasticizers, such as di-2-ethyl-hexyl-phthalate (DEHP), bis(2-ethyl-hexyl) adipate (DEHA), di-octyl adipate (DOA), butyryl-trihexyl-citrate (BTHC), acetyl-tributyl-citrate (ATBC), cyclohexane-1,2-dicarboxylic acid, dibutyl-sebacate (DBS), di-isononyl-ester (DINCH), di-isononyl-phthalate (DINP), di(2-ethyl-hexyl)-terephthalate (DENT), tris(2-ethyl-hexyl) trimellitate (TOTM), and mixtures thereof; radiopaque materials, such as bismuth subcarbonate, bismuth oxychloride, bismuth trioxide, tungsten and barium sulfate; pigments; and dyes.

Each of said biocompatible ingredients can be used in an amount from about 0.01 wt. % and up to 5 wt. %, based on 100 wt. % of said composition (C).

The medical tubing according to the present invention can be manufactured using various processes, including injection moulding and (co)extrusion processes.

Typically, the medical tubing according to the present comprises at least one elongated tubular structure made from composition (C) as defined above, having an internal surface and an external surface; a proximal end; a distal end; and at least one lumen.

Preferably, said medical tubing comprises one, two, three or more lumens.

Said at least one lumen can be advantageously coated with composition (C) according to the present invention.

Preferably, said medical tubing has a wall thickness—measured as the distance between said lumen and said external surface—from 0.1 to 1.5 mm.

Preferably, the at least one lumen has a circular cross section, more preferably having an inner diameter below 1.9 cm, even more preferably below 1.5 cm.

Suitable medical tubing according to the present invention includes catheters for blood transport and delivery, dialysis tubing, enteral feeding systems, oxygen tubing, drainage tubing, peristaltic pump tubing; more in particular, central venous catheters (CVOs), peripherally inserted central catheters (PICCs or PIC lines), arterial lines, ports, renal infusion systems, drainage catheters and haemodialysis catheters.

As mentioned above, the medical tubing according to the present invention can further comprise at least one extension tube, which remains outside the patient's body and which is connected to said at least one elongated tubular structure via a suture wing. The suture wing is typically designed for being attached to the patient's skin, for example via a suture or other suitable mean.

When the medical tubing according to the present invention is a PICC, it typically comprises a clamp and a luer taper at the free end of said extension tube.

Advantageously, the medical tubing according to the present invention is used either to administer a medical substance to or to perform a surgical procedure in at least one cavity, duct or vessel of the human or animal body.

Examples of cavity of the human or animal body comprise the heart chambers, the urinary bladder, the abdominal cavity, the lungs, the uterus.

Examples of duct or vessel of the human or animal body comprise arteries, veins, ureters, the epidural space, the subarachnoid space.

Advantageously, the medical tubing according to the present invention is used in the extracorporeal treatment of a patient's body fluid, preferably of whole blood or plasma.

Advantageously, the medical tubing according to the present invention can be sterilized by suitable physical and chemical method, including notably gamma radiation, electron beam radiation and ethylene oxide sterilization.

Should the disclosure of any patents, patent applications, and publications which are incorporated herein by reference conflict with the description of the present application to the extent that it may render a term unclear, the present description shall take precedence.

The invention will be herein after illustrated in greater detail by means of the Examples contained in the following Experimental Section. The Examples are merely illustrative and are by no means to be interpreted as limiting the scope of the invention.

EXPERIMENTAL SECTION

Materials and Methods:

Monomer (a):

PTMG 1000 Poly(tetramethylene ether)glycol-linear polyether glycol with hydroxyl groups on both ends having molecular weight (Mw) of about 1,000 and hydroxyl value of about 107~118 mg KOH/g.

Monomer (b) having formula:

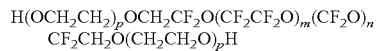

$$H(OCH_2CH_2)_pOCH_2CF_2O(CF_2CF_2O)_m(CF_2O)_n CF_2CH_2O(CH_2CH_2O)_pH$$

with p=1.6, ratio m/n>1 and Mw of about 1,700.

Monomer (c): diphenylen-4,4'-diisocyanate (MDI)

Monomer (d): 1,4-butanediol (BDO)

Catalyst: zinc neodecanoate

Solvents (such as tetrahydro furan) and additives were obtained from Sigma-Aldrich.

PVC medical grade for catheters in form of pellets (having Shore A=74) was obtained from TPV Compound S.r.l. (Italy).

Commercially available PVC bloodline (hereinafter referred to as "catheter") was purchased and used as such.

Weight average molecular weight of the F-TPU polymers was determined by means of gel permeation chromatography (GPC) technique according to the following technique: a solution of the F-TPU polymer was prepared in tetrahydrofuran (THF) at 0.5% wt./vol. concentration; the solution was then centrifuged at 20,000 rpm for 60 minutes at room temperature using a Sorvall RC-6 Plus centrifuge and the supernatant was injected in the GPC apparatus; to correlate retention time and molecular weights, a calibration curve was calculated from narrow standards of polystyrene having molecular weights from 1,700 to 4,000,000 Da.

Preparation of F-TPU Polymers

F-TPU polymer specimen 1 and comparative H-TPU 1 were prepared starting from the abovementioned monomers following the same procedure detailed in Example 15 of U.S. Pat. No. 5,332,798 (AUSIMONT S.P.A.) cited above.

The monomers were used in the molar ratios reported in the following Table 1.

TABLE 1

| Sample | Monomers (molar ratio) | | | |
|---|---|---|---|---|
| | a | b | c | d |
| F-TPU 1 | 0.75 | 0.25 | 3.0 | 2.0 |
| H-TPU 1(*) | 1.0 | — | 3.0 | 2.0 |

(*)comparative

Preparation of the Mixtures 9 g of PVC in the form of pellets and 1 g of F-TPU 1 prepared as disclosed above were added to 40 g of THF under magnetic stirring.

After 1.5 hours at 60° C., an homogenous solution was obtained (herein after referred to as 'Mixture 1').

Using the same procedure, 10 g of PVC pellets were dissolved in 40 g of THF, thus obtaining comparative Mixture 2.

Preparation of Films

Flat homogenous films (having a thickness of about 35 microns) were prepared by filming each of Mixture 1 and Mixture 2 obtained as disclosed above, over a suitable smooth glass support by means of an automatized casting knife. After casting, the solvent was left to evaporate in an oven at 40° C. for 1 hour.

Film 1 was obtained from Mixture 1 according to the present invention.

Comparative Film 2C was obtained from comparative Mixture 2 (pure PVC).

Preparation of a Coated Catheter

A PVC catheter was coated by dipping it in a mixture at 10% by weight of F-TPU 1 in THF and drying it in an oven at 40° C. for 1 hour (Catheter 1).

As comparison, PVC catheter 2C was used as obtained, without the coating.

Example 1

Measurement of Contact Angle (SCA)

The contact angle towards water ($H_2O$) and hexadecane (C16) was evaluated on the films and on the catheters obtained as described above at 25° C. by using the DSA10 instrument (from Krüss GmbH, Germany) according to ASTM D5725-99.

The results are reported in the following Table 2.

TABLE 2

| Sample | Ingredient(s) | Amount (wt. %) | SCA vs. $H_2O$ (°) | SCA vs. C16 (°) |
|---|---|---|---|---|
| Film 1 | PVC | 90 | 107 | 63 |
| | F-TPU 1 | 10 | | |
| Film 2C(*) | PVC | 100 | 93 | 43 |
| Catheter 1 | PVC coated with FTPU 1 | — | 109 | 65 |
| Catheter 2C(*) | PVC | — | 96 | 44 |

(*)comparison

The above results show that Film 1 and Catheter 1 according to the present invention are both more hydrophobic and more oleophobic than Film 2C(*) and Catheter 2C(*), manufactured with pure PVC.

Example 2

Evaluation of the Mechanical Properties

The mechanical properties on Film 1 and Film 2C(*) were assessed at room temperature (23° C.) following ASTM D 638 standard procedure (type V, grip distance=25.4 mm, initial length Lo=21.5 mm). Velocity was set between 1 and 50 mm/min.

The average results obtained for Film 1 and Film 2C prepared as disclosed above are summarized in the following Table 3.

TABLE 3

| Film No. | Stress at break (MPa) | Strain at break (%) |
|---|---|---|
| 1 | 19.2 | 347 |
| 2C(*) | 14.5 | 302 |

(*)comparison

The above results show that Film 1 according to the present invention has improved mechanical properties than Film 2C(*) manufactured with pure PVC.

Example 3

Measurement of Coefficient of Friction (COF)

By using LF Plus Lloyd Dinamometer, the coefficient of friction (COF) test according to ASTM D1894 was carried out on the Films, prepared as described above starting from each of Mixture 1 and Mixture 2.

Three different measurements were performed, and the average value for each Film was evaluated.

The results of static and dynamic COF are reported in following Table 4.

TABLE 4

| Film No. | Static COF | Dynamic COF |
|---|---|---|
| 1 | 1.57 | 0.76 |
| 2C(*) | 2.28 | 0.99 |

(*)comparison

The above results showed that Film 1 according to the present invention had values of COF strongly reduced compared to Film 2C(*).

Example 4

Biocompatibility Tests

The biocompatibility of F-TPU 1 obtained as described above was evaluated using human plasma as follows:

cytotoxicity, by elution test according to ISO 10993-5: 2009 (qualitative and quantitative evaluation);

haemolysis, according to ASTM F756-13 (both direct and indirect contact);

thrombogenicity according to EN ISO10993-4:20017, evaluating PT (Prothrombin time), uPTT (Partial thromboplastin time) and fibrinogen.

The results demonstrated that F-TPU 1 must be considered not cytotoxic, not haemolytic and does not cause alteration in the human plasma.

The invention claimed is:
1. A composition (C) comprising:
(I) at least one melt-processable polymer selected from the group consisting of poly(vinyl chloride) (PVC), polyolefins, polyolefin-based elastomer (POBE) and silicones, and
(II) at least one F-TPU polymer, wherein the F-TPU polymer is at least one fluorinated polyurethane polymer having a weight average molecular weight of from 30,000 to about 150,000 Da, determined by means of gel permeation chromatography (GPC) technique and comprising recurring units derived from:
at least one monomer (b), wherein monomer (b) is at least one hydroxy-terminated (per)fluoropolyether polymer [PFPE polymer] comprising a (per)fluoropolyoxyalkylene chain ($R_{pf}$) having two chain ends, wherein one or more chain ends terminates with at least one —OH group, wherein $R_{pf}$ has the formula:

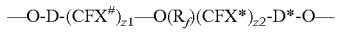
—O-D-$(CFX^\#)_{z1}$—O$(R_f)(CFX^*)_{z2}$-D*-O— wherein z1 and z2, equal or different from each other, are equal to or higher than 1, $X^\#$ and $X^*$, equal or different from each other, are —F or —$CF_3$, provided that when z1 and/or z2 are higher than 1, $X^\#$ and $X^*$ are —F,
D and D*, equal or different from each other, are an alkylene chain comprising from 1 to 6 carbon atom, said alkylene chain being optionally substituted with at least one perfluoroalkyl group comprising form 1 to 3 carbon atoms,
(Rf) comprises repeating units $R^\circ$, said repeating units being independently selected from the group consisting of:
(i) —CFXO—, wherein X is F or $CF_3$,
(ii) —CFXCFXO— wherein X, equal or different at each occurrence, is F or $CF_3$, with the proviso that at least one X is F,
(iii) —$CF_2CF_2CW_2O$—, wherein each of W, equal or different from each other, are F, Cl, or H,
(iv) —$CF_2CF_2CF_2CF_2O$—,
(v) —$(CF_2)_j$—CFZ-O—, wherein j is an integer from 0 to 3 and Z is a group of general formula —O—$R_{(f-a)}$-T, wherein $R_{(f-a)}$ is a fluoroalkylene chain comprising a number of repeating units from 0 to 10, said repeating units selected from the group consisting of —CFXO—, —$CF_2CFXO$—, —$CF_2CF_2CF_2O$—, —$CF_2CF_2CF_2CF_2O$—, with each of X being independently F or $CF_3$ and T being a C1-C3 perfluoroalkyl group;
at least one monomer (c), wherein monomer (c) is at least one aromatic, aliphatic or cycloaliphatic diisocyanate; and
at least one monomer (d), wherein monomer (d) is at least one aliphatic, cycloaliphatic or aromatic diol having from 1 to 14 carbon atoms;
said melt-processable polymer being different from said F-TPU polymer.
2. The composition according to claim 1, wherein said composition (C) comprises said melt-processable polymer in an amount of at least 60 wt. % and of at most 99.99 wt. % based on the total weight of said composition (C).
3. The composition according to claim 1, wherein:
said at least one monomer (b) is a PFPE polymer, wherein the PFPE polymer is the hydroxy-terminated (per)fluoropolyether polymer as defined in claim 1;
said at least one monomer (c) is selected from the group consisting of, 4,4'-methylene diphenylene-di-isocyanate (MDI), 1,6-hexane-diisocyanate (HDI), 2,4-toluene-diisocyanate, 2,6-toluene-diisocyanate, xylylene-diisocyanate, naphthalene-diisocyanate, paraphenylene-diisocyanate, hexamethylene-diisocyanate, isophorone-diisocyanate, 4,4'-dicyclohexyl-methane-diisocyanate and cyclohexyl-1,4-diisocyanate; and
said at least one monomer (d) is selected from the group consisting of ethylene-glycol, 1,4-butanediol (BDO), 1,6-hexane diol (HDO), N,N-diethanolamine and N,N-diisopropanolaniline.
4. The composition according to claim 1, wherein said F-TPU polymer further comprises recurring units derived from at least one monomer (a), wherein monomer (a) is at least one diol selected from the group consisting of polyether type diol, poly-ester type diol, polybutadien-diol and polycarbonate-diol.
5. The composition according to claim 1, wherein said composition (C) comprises said F-TPU polymer in an amount of at least 0.01 wt. % and of at most 40 wt. % based on the total weight of said composition (C).
6. The composition according to claim 1, wherein said composition (C) comprises at least one further ingredient selected from the group consisting of: plasticizers; radiopaque materials; pigments; and dyes.
7. The composition according to claim 6, wherein each further ingredient is used in an amount from about 0.01 wt. % and up to 5 wt. %, based on 100 wt. % of said composition (C).
8. An article obtained from a composition (C) as defined in claim 1.
9. The article according to claim 8, wherein said article is a medical tubing.
10. The article of claim 9, wherein said medical tubing is selected from in the group consisting of catheters for blood transport and delivery, dialysis tubing, enteral feeding systems, oxygen tubing, drainage tubing, peristaltic pump tubing, central venous catheters (CVCs), peripherally inserted central catheters (PICCs or PIC lines), arterial lines, ports, renal infusion systems, drainage catheters and haemodialysis catheters.
11. A method for administering a medical substance to at least one cavity, duct or vessel of the human or animal body, said method comprising the use of the medical tubing as defined in claim 9.
12. A method for performing a surgical procedure in at least one cavity, duct or vessel of the human or animal body, said method comprising the use of a medical tubing as defined in claim 9.
13. A method for the extracorporeal treatment of a patient's body fluid, said method comprising the use of a medical tubing obtained from composition (C) as defined in claim 9.
14. The composition according to claim 6, wherein said plasticizer is selected from di-2-ethyl-hexyl-phthalate (DEHP), bis(2-ethyl-hexyl) adipate (DEHA), di-octyl adipate (DOA), butyryl-trihexyl-citrate (BTHC), acetyl-tributyl-citrate (ATBC), cyclohexane-1,2-dicarboxylic acid, dibutyl-sebacate (DBS), di-isonyl-ester (DINCH), di-isononyl-phthalate(DINP), di(2-ethyl-hexyl)-terephthalate (DEHT), tris(2-ethyl-hexyl) trimellitate (TOTM), or mixtures thereof; and
wherein said radiopaque material is selected from bismuth subcarbonate, bismuth oxychloride, bismuth trioxide, tungsten or barium sulphate, or mixtures thereof.
15. The article according to claim 9, wherein said medical tubing comprises at least one elongated tubular structure having an internal surface and an external surface; a proximal end; a distal end; and at least one lumen.

* * * * *